(12) United States Patent
Chu

(10) Patent No.: US 9,566,010 B2
(45) Date of Patent: Feb. 14, 2017

(54) METHOD FOR DETECTING CARDIAC STATUS, METHOD FOR MONITORING CARDIAC STATUS DURING EXERCISE, AND APPARATUS FOR MONITORING CARDIAC STATUS

(71) Applicant: National Defense Medical Center, Taipei (TW)

(72) Inventor: Chi Ming Chu, Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 0 days.

(21) Appl. No.: 14/838,337

(22) Filed: Aug. 27, 2015

(65) Prior Publication Data

US 2016/0058314 A1    Mar. 3, 2016

(30) Foreign Application Priority Data

Sep. 1, 2014    (TW) .............................. 103130141 A

(51) Int. Cl.
*A61B 5/02*    (2006.01)
*A61B 5/024*    (2006.01)
*A61B 5/11*    (2006.01)
*A61B 5/00*    (2006.01)

(52) U.S. Cl.
CPC .......... *A61B 5/02438* (2013.01); *A61B 5/1118* (2013.01); *A61B 5/7275* (2013.01)

(58) Field of Classification Search
CPC ...... A61B 5/02438; A61B 5/1118; A61B 5/11
See application file for complete search history.

(56) References Cited

U.S. PATENT DOCUMENTS

2016/0007935 A1*   1/2016  Hernandez .......... A61B 5/7278
                                                        600/301

* cited by examiner

*Primary Examiner* — Robert N Wieland
(74) *Attorney, Agent, or Firm* — Leong C. Lei

(57) ABSTRACT

A method for detecting cardiac status is provided. A user's heart rate is measured by a heart rate detection unit, and the user's acceleration or activity level is measured by an acceleration detection unit, which the activity level is calculated by the acceleration detection unit. A cardio force index is obtained by a calculating unit based on the heart rate, and the acceleration, or the weight as the following formula (Ia) or (Ib):

$$CFI = (Weight \times) Acceleration / Heart\ Rate \quad (Ia)$$

$$CFI = (Weight \times) Activity\ Level / Heart\ Rate \quad (Ib)$$

The cardio force ratio is a ratio of the user as the following formula (II):

$$Cardio\ Force\ Ratio = CFI\ of\ Exercise / CFI\ of\ Walking \quad (II)$$

A method for monitoring cardiac status during exercise and an apparatus for monitoring cardiac status are also provided.

4 Claims, 2 Drawing Sheets

METHOD FOR DETECTING CARDIAC STATUS, METHOD FOR MONITORING CARDIAC STATUS DURING EXERCISE, AND APPARATUS FOR MONITORING CARDIAC STATUS

TECHNICAL FIELD OF THE INVENTION

The present invention relates generally to a method for detecting cardiac status, a method for monitoring cardiac status during exercise, and an apparatus for monitoring cardiac status, and more particularly to a real-time and non-invasive method for detecting a cardiac status, a method for monitoring a cardiac status during exercise, and an apparatus for monitoring a cardiac status.

DESCRIPTION OF THE PRIOR ART

Exercise is getting increasingly popular and, particularly, road running or Marathon is becoming a sport for most of people. The number of accidents of sudden death is gradually increased for self training of running or jogging. Most of the causes for such accidents are that people are not aware of the cardiac status or cardiac loading condition so as to suffer sports injury or even sudden death. Furthermore, in military medicine, precautions can be made for people having uncomfortable situations, such as cardiac muscle flutter and myocardial infarction, caused by physical training by monitoring training intensity and cardiac status of people.

However, conventional monitoring systems, such as heart rate bands, exercise watches, and wearable technology, provide instantaneous information only relating to physiological parameters of heart rate, respiration rate, blood pressure, distance, and location. Users cannot get aware of the cardiac status and cardiac loading condition from those physiological parameters. Consequently, the users cannot realize the status of their own hearts with the conventional monitoring systems. In addition, no data or reading is provided to indicate the loading condition of the heart of a user so that there is no way for the use to adjust the way and intensity of exercise and consequently, sports injury may be caused.

Further, one of the most important clinic indexes for reflecting the cardiac functionality is cardiac output (CO), which indicates the amount of blood that is pumped by the heart to the peripheral circulatory system. The cardiac output may show the functional status of the entire circulatory system with which the loading of the heart can be realized. However, the cardiac output can only be detected through a static ultrasonic technique, so it is not possible to acquire an instantaneous cardiac status during exercise by means of cardiac output.

In view of the above, it is a vital issue to allow a user to get timely aware of the cardiac status.

SUMMARY OF THE INVENTION

In an aspect of the present invention, a method for detecting cardiac status is provided, comprising obtaining a user's weight. Then, the user's heart rate is measured by a heart rate detection unit, and the user's acceleration or activity level is measured by an acceleration detection unit, wherein the activity level is calculated by the acceleration detection unit based on the acceleration.

A cardio force index (CFI) is calculated by a calculating unit according to the weight, the heart rate, and the acceleration or the activity level with the following formula (Ia) or (Ib):

$$CFI = Weight \times Acceleration / Heart\ Rate \quad (Ia)$$

$$CFI = Weight \times Activity\ Level / Heart\ Rate \quad (Ib)$$

wherein the CFI indicates force per heartbeat of the user.

According to an embodiment of the present invention, the measurement of the heart rate of the user by the heart rate detection unit is conducted by detecting heartbeat of the user or the pulse of an artery of the user.

According to an embodiment of the present invention, the weight has a unit of kilogram (kg), the heart rate is heartbeats per second, and the acceleration has a unit of meter per square second ($m/s^2$).

In another aspect of the present invention, a method for monitoring cardiac status during exercise is provided, comprising obtaining CFIs of walking and exercise of the user with the above-discussed method for detecting cardiac status and calculating a cardio force ratio by the calculating unit with the following formula (II):

$$Cardio\ Force\ Ratio = CFI\ of\ Exercise / CFI\ of\ Walking \quad (II)$$

According to an embodiment of the present invention, the cardio force ratio is calculated by the calculating unit with the following formula (IIIa) or (IIIb):

$$Cardio\ Force\ Ratio = (Acceleration\ of\ Exercise \times Heart\ Rate\ of\ Walking)/(Heart\ Rate\ of\ Exercise \times Acceleration\ of\ Walking) \quad (IIIa)$$

$$Cardio\ Force\ Ratio = (Activity\ Level\ of\ Exercise \times Heart\ Rate\ of\ Walking)/(Heart\ Rate\ of\ Exercise \times Activity\ Level\ of\ Walking) \quad (IIIb)$$

According to an embodiment of the present invention, the method for monitoring cardiac status during exercise further comprises alarming the user with an alarm unit when the cardio force ratio exceeds a threshold.

In a further aspect of the present invention, an apparatus for monitoring cardiac status is provided, comprising a heart rate detection unit, an acceleration detection unit, and a calculating unit. The heart rate detection unit measures heart rate of a use. The acceleration detection unit measures acceleration or activity level of the user, wherein the activity level is calculated by the acceleration detection unit based on the acceleration. The calculating unit calculates a CFI and a cardio force ratio according to the weight, the heart rate, and the acceleration or the activity level of the user wherein the CFI is calculated with the following formula (Ia) or (Ib):

$$CFI = Weight \times Acceleration / Heart\ Rate \quad (Ia)$$

$$CFI = Weight \times Activity\ Level / Heart\ Rate \quad (Ib)$$

and the cardio force ratio is a ratio between a CFI of exercise and a CFI of walking of the user and is calculated with the following formula (II):

$$Cardio\ Force\ Ratio = CFI\ of\ Exercise / CFI\ of\ Walking \quad (II)$$

According to an embodiment of the present invention, the apparatus for monitoring cardiac status further comprises an alarm unit, wherein when the cardio force ratio exceeds a threshold, the alarm unit issues an alarm to the user.

According to an embodiment of the present invention, the apparatus for monitoring cardiac status further comprises a memory unit, which stores therein the CFI, the cardio force ratio, and time, location, and associated parameters of the user during exercise.

According to an embodiment of the present invention, the apparatus for monitoring cardiac status further comprises a positioning unit, through which a position of the user is acquired.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by illustrative examples.

DETAILED DESCRIPTION OF THE PREFERRED EMBODIMENTS

Figure 1:
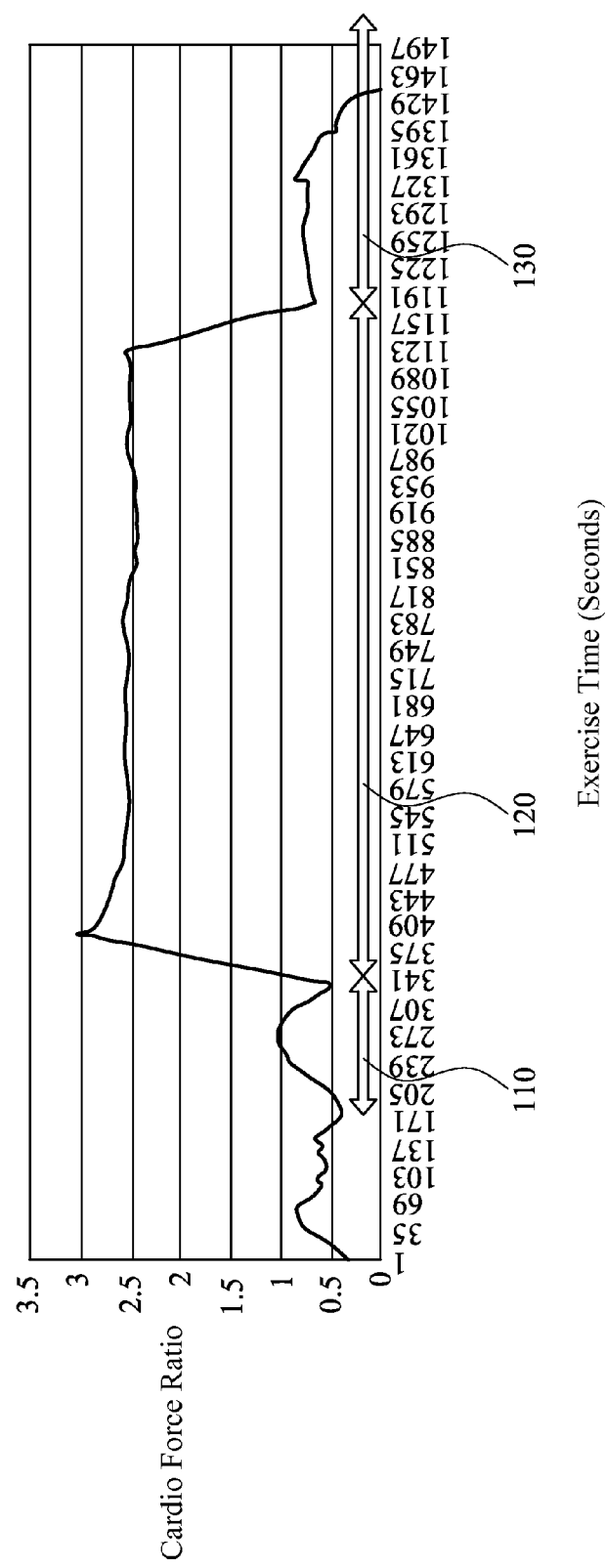
FIG. 1 shows a relationship between a cardio force ratio of a person having a strong cardio force and time according to an embodiment of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The present invention provides a method for detecting cardiac status, which comprises obtaining a user's weight. Then, the user's heart rate is measured by a heart rate detection unit, and the user's acceleration or activity level is measured by an acceleration detection unit, wherein the activity level is calculated by the acceleration detection unit based on the acceleration. The body weight, the heart rate, and the acceleration or the activity level are calculate to cardio force index (CFI) by a calculating unit with the following formula (Ia) or (Ib):

$$\text{Cardio Force Index} = \text{Weight} \times \text{Acceleration}/\text{Heart Rate} \quad (\text{Ia})$$

$$\text{Cardio Force Index} = \text{Weight} \times \text{Activity Level}/\text{Heart Rate} \quad (\text{Ib})$$

The cardio force index (CFI) is a novel index relating to cardiac status, which indicates the force per heartbeat of the user. The force that acts on the user is calculated with Newton's second law of motion (F=ma) and the force acting on the user is divided by heart rate to calculate the force per heartbeat of the user. The present invention provides a CIF, in which the weight, the heart rate, and the acceleration of a user are used to calculate the CFI, so that the user may realize and inspect his or her own instantaneous cardiac status. The heart rate and acceleration vary with the physiological conditions of the user, time, and location. Further, with the extension of a training period, the cardiopulmonary capability of the user is improved so that the rate of heart beating may become slower. Thus, it is generally meaningless to determine the cardiac loading simply based on heart rate and acceleration. The present invention provides a method that combines heart rate and acceleration to convert simple physiological parameters into a meaningful index of cardio force, the CFI.

Measuring the heart rate of the user with the heart rate detection unit may be conducted by using the heart rate detection unit to detect the beating of the user's heart or the pulse of an artery of the user, and the measurement can be done in any feasible way, such as detecting the blood flow in a capillary vessel of a finger tip or an earlobe, detecting an electrocardiographic signal of a palm area, or detecting an electrocardiographic signal of a chest area with electrodes. Thus, in formula (I), heart rate that is used for calculation of CFI is the number of heartbeats or the number of artery pulses in unit time.

The acceleration detection unit detects the acceleration or the activity level of the user, wherein the activity level is calculated by the acceleration detection unit based on the acceleration and provides a figure related to the acceleration. In addition to the detection of acceleration, the acceleration detection unit may also be used to measure a parameter related to an activity of the user and the activity level may be calculated according to the acceleration and the other related parameter. The activity level of the user during exercise may be detected across various platforms or measured with equipment of various forms, such as a pedometer, an application program (APP), heart rate meter, and a heart rate belt.

In an embodiment, the unit of weight is kilogram (kg), that of heart rate is heartbeats per second, and that of acceleration is meter per square second (m/s$^2$).

The present invention also provide a method for monitoring cardiac status during exercise, which comprises applying the above formula (I) to obtain a user's CFI during walking or exercise and using a calculating unit to obtain a cardio force ratio, which is calculated with the following formula (II):

$$\text{Cardio Force Ratio} = \text{CFI of Exercise}/\text{CFI of Walking} \quad (\text{II})$$

The cardio force ratio is the ratio of heart pumping power of a user between exercises and walking into a unitless number. The user may get aware of his or her own cardiac loading condition with the cardio force ratio and may set up a reference of loading that his or her heart may bear during exercise.

The cardio force ratio is a ratio between a user's CFI values for walking and exercise and this may eliminate differences among individual users, such as differences between different users resulting from the difference of height and weight. Thus, the cardio force ratio may provide a reference for comparison among different users. Further, since the cardio force ratio is a ratio between CFIs, it eliminates errors caused by the heart rate detection unit and the acceleration detection unit being set up at different locations so that the heart rate detection unit and the acceleration detection unit do not need to be set at the same locations for each time of operation.

When the cardio force ratio exceeds a preset threshold, this means the heart of the user cannot bear the loading. Since the loading condition of the heart of each user may be different, the threshold is generally determined according to the cardiac status of the user. In an exercise period, the heart is pressurizing for an extended period of time, generally speaking, in a steady exercise condition, the cardio force ratio maintains in a specific range for tens of minutes. When the cardio force ratio exceeds the threshold, this means the heart of the user is no longer capable of the mode and intensity of exercise that are currently taken. The threshold is generally higher than the cardio force ratio of a steady exercise condition.

It is noted that since the weight of a user hardly changes between walking and exercise, in an embodiment, the cardio force ratio is taken as the ratio heart rate and acceleration between a walking condition and an exercise condition. The cardio force ratio is calculated with the following formula (IIIa):

Cardio Force Ratio=(Acceleration of Exercise×Heart Rate of Walking)/(Heart Rate of Exercise×Acceleration of Walking)  (IIIa)

The above formula (III) is based on formulas (I) and (II) and is obtained through conversion with the following formulas:

Cardio Force Ratio=[(Weight×Acceleration of Exercise)/Heart Rate of Exercise]/[(Weight×Acceleration of Walking)/Heart Rate of Walking]= (Acceleration of Exercise/Heart Rate of Exercise)/(Acceleration of Walking/Heart Rate of Walking)=(Acceleration of Exercise×Heart Rate of Walking)/(Heart Rate of Exercise×Acceleration of Walking)

In another embodiment, the cardio force ratio is taken as a ratio of heart rate and the activity level between a walking condition and an exercise condition. The cardio force ratio is calculated with the following formula (IIIb):

Cardio Force Ratio=(Activity Level of Exercise× Heart Rate of Walking)/(Heart Rate of Exercise×Activity Level of Walking)  (IIIb)

The cardio force ratio does not concern about the weight of the user so that it can be obtained with various platforms and various forms of equipment.

In an embodiment, the method for monitoring cardiac status during exercise further comprises issuing an alarm to the user with an alarm unit when the cardio force ratio exceeds the threshold. The way of alarming a user can be a visual, audio, or tactile alarm, such as making a sound, a lighting signal, or vibrations.

The method for monitoring cardiac status during exercise according to the present invention is applicable to monitoring the cardiac status for any kind of exercise, such as walking, jogging, running, marathon, cycling, swimming, and upward and downward motions including climbing stairs and slopes.

Conventional monitoring devices provide instantaneous information only relating to physiological parameters of heart rate, respiration rate, blood pressure, distance, and location. Users cannot be informed, from these physiological parameters of whether the heart can bear the intensity and mode of exercise that are currently taken; this is not quite meaningful for the user. Further, heretofore, the inspection of cardiac capability is primarily based on static cardiac ultrasonic technique and no real time data or information can be acquired during exercise. The present invention provides a novel method for detecting cardiac status, wherein the weight, the acceleration, and the heart rate of a user are used to calculate an instantaneous value of CFI of the user (which is the force per heartbeat of the user) so that the physiological parameter is converted into a meaningful index. Further, The present invention also provides a method for monitoring cardiac status during exercise, wherein the CFI of walking is taken as a reference and the multiple of the CFI of exercise with respect to that of walking (this being the cardio force ratio) is calculated so that the cardio force ratio may serve as a standard for judging the loading of the heart. The method for detecting cardiac status and the method for monitoring cardiac status during exercise according to the present invention may be used to allow a user to realize the force per heart beat with the CFI value and also to realize the current cardiac status with the cardio force ratio and to determine if the heart can bear the current intensity and mode of exercise. The present invention provides methods that allow for continuous and non-invasive detection and monitoring of the cardiac status so as to expand the inspection of cardiac capability from a static way of inspection to a dynamic fashion of physical capability monitoring.

The present invention also provides an apparatus for monitoring cardiac status, which comprises a heart rate detection unit, an acceleration detection unit, and a calculating unit. The heart rate detection unit measures the heart rate of a user. The acceleration detection unit measures the acceleration or the activity level of the user, wherein the activity level is calculated by the acceleration detection unit based on the acceleration. The calculating unit calculates and obtains a cardio force index (CFI) and the cardio force ratio according to the weight, the heart rate, and the acceleration or the activity level of the user. CFI is calculated with the following formula (Ia) or (Ib):

Cardio Force Index=Weight×Acceleration/Heart Rate  (Ia)

Cardio Force Index=Weight×Activity Level/Heart Rate  (Ib)

The cardio force ratio is a ratio between the CFI of walking and the CFI of exercise of a user and is calculated with the following formula (II):

Cardio Force Ratio=CFI of Exercise/CFI of Walking  (II)

When the cardio force ratio exceeds a preset threshold, this means the heart of the user cannot bear the current exercise intensity. The user must, at this moment, reduce the exercise intensity in order to prevent exceeding the loading capacity of the heart. Since the loading capacity of the heart of each user may be different, a threshold of cardio force ratio is determined according to the cardiac status of the user. Generally speaking, in a steady exercise condition, the cardio force ratio maintains in a specific range and the threshold is set higher than this specific range.

It is noted that the cardio force ratio does not concern the weight of the user and may be acquired and obtained with various platforms and various forms of equipment. Being not involved with the weight of the user, the cardio force ratio can be calculated with the above-mentioned formula (IIIa) or (IIIb).

The heart rate detection unit detects the heart rate of the user and can be of any form, such as a chest band, a vest, and a patch.

The acceleration detection unit detects the acceleration of the user during a movement and can be of an accelerometer of any form, such as a three-axis accelerometer, a nine-axes accelerometer, a sixteen-axis accelerometer, and a G-sensor.

The heart rate detection unit and the acceleration detection unit can be connected with each other in a wired form or a wireless manner. The wireless connection can be such as Bluetooth, ZigBee, Wifi, very high frequency (VHF), FM, or AM.

The apparatus for monitoring cardiac status of the present invention can be stand-alone device or be operable with connection with a host device.

When the apparatus for monitoring cardiac status of the present invention is operating independently as a stand-alone device, the apparatus of the present invention converts heartbeats, acceleration, cardiac force index, and/or cardiac force ratio into signals that are transmitted out from the apparatus to allow the user to determine the current cardiac status according those transmitted signals In the instant embodiment, the apparatus for monitoring cardiac status according to the present invention comprises a buzzer. Based on the settings of the buzzer, the user may be notified of the current conditions of heartbeats, acceleration, cardiac force index, and/or cardiac force ratio. For example, the buzzer can be set to give off sounds of different frequencies to allow the user to determine the current heartbeats, acceleration, cardiac force index, and/or cardiac force ratio according to the frequency emitting from the buzzer.

When the apparatus for monitoring cardiac status of the present invention is put into operation in connection with a host device, the apparatus of the present invention transmits CFI and the cardio force ratio to the host device so that the user may get aware of the cardiac status through the host device. In the instant embodiment, the apparatus for monitoring cardiac status according to the present invention comprises a transmission unit and a display unit. The transmission unit transmits signals (such as CFI and the cardio force ratio) to the display unit. The signals can be transmitted from the transmission unit to the display unit in a wireless manner or a wired manner. The wired manner can be such as universal serial bus (USB). The display unit can be of any form, such as a wristwatch display, a near-eye display, a mobile device, and a computer.

The apparatus for monitoring cardiac status according to the present invention may comprise an alarm unit. When the cardio force ratio exceeds a threshold, the alarm unit issues an alarm to the user. At this moment, the user should reduce the intensity of exercise in order to maintain the cardio force ratio not exceeding the threshold. The alarm issued by the alarm unit to the user may include an audio alarm or a visual alarm. In an embodiment, the alarm unit comprises a buzzer. When the cardio force ratio exceeds the threshold, the buzzer gives off a sound to alarm the user. In another embodiment, the alarm unit comprises a lighting alarm unit, which issues a light alarm to the user when the cardio force ratio exceeds the threshold.

The apparatus for monitoring cardiac status according to the present invention may comprises a memory unit that store CFI and cardio force ratio of a user and time, location, and other associated parameters of the user during exercise. The memory unit can be of any form, such as a flash memory. The user may realize and observe, with the memory unit, his or her cardiac status in different time periods. The memory unit may additionally store CFI of walking of the user so that after the device has been set up in the first time operation, there is no need for re-setting or re-configuring the apparatus.

The apparatus for monitoring cardiac status according to the present invention may comprise a positioning unit, so that the position of the user may be acquired with the positioning unit. For example, in case of accident occurring when the user is doing exercise or training so that the user cannot communicate with the others, the location of the user may be searched and identified with the positioning unit. The positioning unit can be of any form, such as a global positioning system (GPS).

In an embodiment, the apparatus for monitoring cardiac status according to the present invention may emit wireless signals. For example, when the outside cannot get into contact with the user, the apparatus of the present invention may issue a signal so that the outside may get aware of the location of the user through the very high frequency. Thus, the apparatus of the present invention may serve as a searching and rescuing measure.

The apparatus for monitoring cardiac status according to the present invention may comprise a processing unit, which is operable to determine the exercise condition of a user according to the moving speed and the heartbeat of the user. For example, when the user is walking, the heart rate does not vary much and the processing unit can determine the period is a walking period and CFI of this period may be taken as a reference for calculation of the cardio force ratios of other time periods. As another example, when the user is riding a transportation vehicle, since the speed of the user is increased but the heart beating does not, the processing unit determines that the user is moved with machine power.

In an embodiment, a transmission unit transmits the CFI and the cardio force ratio to a display unit. Such an apparatus for monitoring cardiac status can be used to monitor, in a real-time manner, the cardiac status of the user himself or herself. The user may get instantaneously aware of his or her own CFI and cardio force ratio from the display unit and may modify or change the exercise intensity according to the data.

In another embodiment, the apparatus of the present invention is carried by each of a number of users. Each of the apparatuses comprises a transmission unit. The CFI and the cardio force ratio of each of the users may be transmitted through the transmission unit carried thereby to a common display unit. Thus, the apparatus for monitoring cardiac status according to the present invention can be used to monitor the cardiac status of a number of users and the cardiac status of each user can be known from the display unit. For example, during military physical training, the apparatus is carried by each trainee and the CFI and the cardio force ratio of each of the trainees can be transmitted through the transmission units to a common display unit. The trainer may get aware of individual cardiac status from the common display unit and modify or change the training intensity of each of the trainees according to the data.

The apparatus for monitoring cardiac status according to the present invention can be a waterproof apparatus for monitoring cardiac status.

The apparatus for monitoring cardiac status according to the present invention can be combined with an application program of a mobile device. A user may get instantaneously aware of his or her CFI and cardio force ratio with the application program and realize the cardiac loading condition in order to modify or change the mode and intensity of exercise.

The apparatus for monitoring cardiac status according to the present invention is a portable, non-invasive apparatus, and real-time apparatus for monitoring cardiac status, allowing a user to immediately realize his or her own cardiac loading during exercise in order to adjust the way, intensity, and frequency of exercise for keeping exercise safety. The apparatus for monitoring cardiac status according to the present invention is also applicable to military training to allow each trainee to realize individual cardiac status in order to adjust or modify the training intensity of the trainee.

The method of the present invention will be further explained hereinafter with reference to embodiments thereof. However, the description given herein is provided for illustration only and is not intended to limit the scope of the present invention. The scope of protection that is sought for the present invention is only defined by the appended claims.

Referring to FIG. 1, a relationship between the cardio force ratio of a person having a strong cardio force and time is illustrated according to an embodiment of the present invention. In the instant embodiment, a representative user is aged 22 and has a powerful heart. The user uses the method and apparatus for monitoring cardiac status during exercise according to the present invention and various activities have been taken, including a walking period 110, a running period 120, and a post-running period 130. In the running period 120, data are obtained with the user slowly running for a distance of 3000 meters. The post-running period 130 is a period after the running of the user has been ended. FIG. 1 uses the maximum CFI of the walking period 110 to serve as a reference for calculation of the cardio force ratios of the other time periods. The relationship between the cardio force ratio and time is plotted. Thus, FIG. 1 shows the cardio force ratio of the user varies with the change of activity. The signals before the starting of the walking period 110 are noises.

When the user changes from the walking period 110 to the running period 120, the user is converted from a relatively static condition of walking into a dynamic condition of running. Since the acceleration of the user increases, the cardio force ratio is quickly increased to thereby reach an explosive peak. The explosive peak indicates the explosive power of the user and in FIG. 1, this period shows a cardio force ratio of around 3. After the explosive peak, the cardio force ratio starts lowering and after a lapse of time, the cardio force ratio becomes moderate and gentle and enters an endurance period, where the cardio force ratio is around 2.5. After the running period 120 has been ended, the post-running period 130 starts. At this moment, the dynamic condition of running of the user is ended so that the acceleration is reduced very quickly and the cardio force ratio also lowers.

Figure 2:
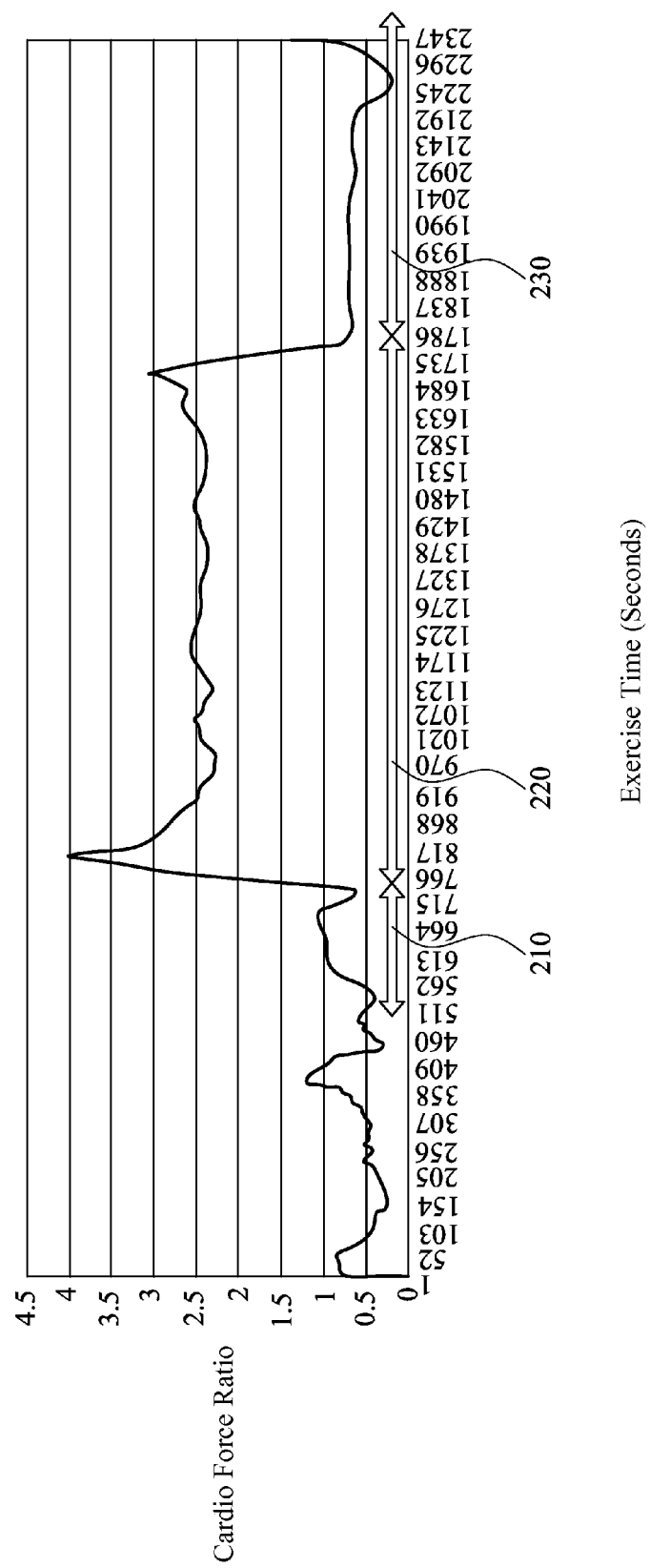
FIG. 2 shows a relationship between a cardio force ratio of a person having a weak cardio force and time according to another embodiment of the present invention.

Referring to FIG. 2, a relationship between the cardio force ratio of a person having a weak cardio force and time is illustrated according to an embodiment of the present invention. In the instant embodiment, the user is aged 42, who, compared to the user of age 22 (FIG. 1), has a weak heart. Similar to FIG. 1, the user uses the method and apparatus for monitoring cardiac status during exercise according to the present invention and various activities have been taken, including a walking period 210, a running period 220, and a post-running period 230. In the running period 220, data are obtained with the user slowly running for a distance of 3000 meters. The post-running period 230 is a period after the running of the user has been ended. FIG. 2 uses the maximum CFI of the walking period 210 to serve as a reference for calculation of the cardio force ratios of the other time periods. The relationship between the cardio force ratio and time is plotted. Thus, FIG. 2 shows the cardio force ratio of the user varies with the change of activity. The signals before the starting of the walking period 210 are noises.

When the user changes from the walking period 210 to the running period 220, the user is converted from a relatively static condition of walking into a dynamic condition of running. Since the acceleration of the user increases, the cardio force ratio is quickly increased to thereby reach an explosive peak. The explosive peak indicates the explosive power of the user and in FIG. 2, this period shows a cardio force ratio of around 4. After the explosive peak, the cardio force ratio starts lowering and after a lapse of time, the cardio force ratio becomes moderate and gentle and enters an endurance period, where the cardio force ratio is around 2.5. After the running period 220 has been ended, the post-running period 230 starts. At this moment, the dynamic condition of running of the user is ended so that the acceleration is reduced very quickly and the cardio force ratio also lowers.

It can be known from FIGS. 1 and 2, the method and the apparatus for monitoring cardiac status during exercise according to the present invention can be used to observe, in a dynamic and continuous manner, the cardiac status of a user.

Based on the same theory, the present invention is also applicable to monitoring the status of a prime mover (such as an engine) of a moving object (such as an automobile). In an embodiment, a method for monitoring a status of a prime mover when a moving object is moving comprises:

operating an calculating unit to obtain a loading index and a loading ratio according to weight of the moving object, rotational speed of the prime mover, and acceleration of the moving object or activity level of the moving object, wherein the loading index is calculated with the following formula (Ia) or (Ib):

$$\text{Loading Index} = \text{Weight of Moving Object} \times \text{Acceleration of Moving Object} / \text{Rotational Speed of Prime Mover} \quad \text{(Ia)}$$

$$\text{Loading Index} = \text{Weight of Moving Object} \times \text{Activity Level of Moving Object} / \text{Rotational Speed of Prime Mover} \quad \text{(Ib)}$$

The loading ratio is the ratio between the loading index of the moving object in movement and the loading index of idling and is calculated with the following formula (II):

$$\text{Loading Ratio} = \text{Loading Index of Movement} / \text{Loading Index of Idling} \quad \text{(II)}$$

As a further example of application, the present invention provides a model, which is based on the cardio force index, the cardio force ratio, or variation of the cardio force index or the cardio force ratio, for predicting the correlation between the time required for a person to complete running through a predetermined distance (such as 3,000 meters) and whether the person is considered qualifying for such a test. As such, the present invention is applicable to determine or predict the time required for completing movement of a target so as to precaution and predict the possibility of accident events thereby reducing the potential risk of safety and preventing unexpected occurrence of excessive exercise loading to the hearts during running.

In summary, the present invention provides a method for detecting cardiac status, which calculate the instantaneous CFI of the user by using the weight, the heart rate, and the acceleration or the activity level of the user in order to transform physiological parameters, which each individually are not quite meaningful, into CFI that is more meaningful. The CFI is provided for detecting, in a dynamic manner, the cardiac status of the user.

Further, The present invention provides a method for monitoring cardiac status during exercise, which uses the CFI of walking of the user as a reference to obtain the ratio of between the CFI of exercise and that of walking (this being a cardio force ratio) to provide a standard for determining if the heart is capable of the exercise. Since the cardio force ratio is simply a ratio, it helps eliminates individual differences among the users and errors caused by changing the location of the detection units.

Further, the present invention provides an apparatus for monitoring cardiac status that is a portable, non-invasive, and real-time apparatus for monitoring cardiac status, allowing a user to immediately realize the cardiac loading during exercise in order to adjust or modify the way, intensity, and frequency of exercise for keeping exercise safety. The apparatus for monitoring cardiac status according to the present invention is applicable to all sorts of training or competition so that the trainers may get aware of the cardiac status of each trainee and adjust the training intensity of the trainee.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. An apparatus for monitoring cardiac status, comprising:
a heart rate detection unit, which measures heart rate of a user;
an acceleration detection unit, which measures acceleration or activity level of the user, wherein the activity level is calculated by the acceleration detection unit based on the acceleration; and
a calculating unit, which calculates a cardio force index (CFI) and a cardio force ratio according to the weight, the heart rate, and the acceleration or the activity level of the user,
wherein the CFI is calculated with the following formula (Ia) or (Ib):

$$CFI = Weight \times Acceleration / Heart\ Rate \qquad (Ia)$$

$$CFI = Weight \times Activity\ Level / Heart\ Rate \qquad (Ib)$$

and the cardio force ratio is a ratio between a CFI of exercise and a CFI of walking of the user and is calculated with the following formula (II):

$$Cardio\ Force\ Ratio = CFI\ of\ Exercise / CFI\ of\ Walking \qquad (II).$$

2. The apparatus according to claim 1 further comprising an alarm unit, wherein when the cardio force ratio exceeds a threshold, the alarm unit issues an alarm to the user.

3. The apparatus according to claim 1 further comprising a memory unit, which stores therein the CFI, the cardio force ratio, and time, location, and associated parameters of the user during exercise.

4. The apparatus according to claim 1 further comprising a positioning unit, through which a position of the user is acquired.

* * * * *